US012402004B2

(12) United States Patent
Kothandaraman et al.

(10) Patent No.: US 12,402,004 B2
(45) Date of Patent: Aug. 26, 2025

(54) METHODS AND SYSTEMS FOR MANAGING ACCESS TO IMPLANTABLE MEDICAL DEVICES

(71) Applicant: Boston Scientific Neuromodulation Corporation, Valencia, CA (US)

(72) Inventors: Sridhar Kothandaraman, Valencia, CA (US); Berj Doudian, Sun Valley, CA (US); Chirag Shah, Valencia, CA (US); Joshua Uyeda, Los Angeles, CA (US); Keron Greene, Lancaster, CA (US)

(73) Assignee: Boston Scient ation Corporation, Valencia, CA (US)

( * ) Notice: Subject to any disclaimer, the term of this patent is extended or adjusted under 35 U.S.C. 154(b) by 344 days.

(21) Appl. No.: 17/513,240

(22) Filed: Oct. 28, 2021

(65) Prior Publication Data
US 2022/0141663 A1  May 5, 2022

Related U.S. Application Data

(60) Provisional application No. 63/109,749, filed on Nov. 4, 2020.

(51) Int. Cl.
*H04W 12/08* (2021.01)
*A61N 1/372* (2006.01)
(Continued)

(52) U.S. Cl.
CPC ........ *H04W 12/08* (2013.01); *A61N 1/37254* (2017.08); *G16H 40/40* (2018.01);
(Continued)

(58) Field of Classification Search
CPC ........... A61N 1/37235; A61N 1/37254; G16H 40/40; G16H 40/67; H04L 63/068;
(Continued)

(56) References Cited

U.S. PATENT DOCUMENTS 5,792,204 A   8/1998 Snell
6,181,969 B1  1/2001 Gord
(Continued)

OTHER PUBLICATIONS

Invitation to Pay Additional Fees and, Where Applicable, Protest Fee for PCT Application No. PCT/US2021/057018 mailed Mar. 3, 2022.
(Continued)

*Primary Examiner* — Thomas J Dailey
(74) *Attorney, Agent, or Firm* — Branch Partners PLLC; Bruce E. Black

(57) ABSTRACT

An external device for wireless communication with an implantable medical device can include a memory having stored thereon instructions for a first application and authentication credentials specific to the first application; and a processor configured for transmitting the authentication credentials specific to the first application to an implantable medical device to authorize access to the implantable medical device by the first application. An external device for wireless communication with an implantable medical device can include a memory including authentication credentials stored thereon; and a processor configured for transmitting the authentication credentials to an implantable medical device to authorize access; receiving a request to facilitate authorization of the second device and receiving second authentication credentials from the second device; determining authentication or authorization of the second device; and transmitting a token or authorization credentials directing the implantable medical device to authorize access by the second device.

20 Claims, 8 Drawing Sheets

(51) Int. Cl.
*G16H 40/40* (2018.01)
*G16H 40/67* (2018.01)
*H04L 9/40* (2022.01)
*H04W 12/043* (2021.01)
*H04W 12/069* (2021.01)
*H04W 12/33* (2021.01)
*H04W 12/61* (2021.01)
*H04W 12/71* (2021.01)

(52) U.S. Cl.
CPC .......... *G16H 40/67* (2018.01); *H04W 12/069* (2021.01); *H04W 12/61* (2021.01); *A61N 1/37235* (2013.01); *H04L 63/068* (2013.01); *H04L 63/0823* (2013.01); *H04W 12/043* (2021.01); *H04W 12/33* (2021.01); *H04W 12/71* (2021.01)

(58) Field of Classification Search
CPC ............ H04L 63/0823; H04W 12/043; H04W 12/069; H04W 12/08; H04W 12/33; H04W 12/61; H04W 12/71
See application file for complete search history.

(56) References Cited

U.S. PATENT DOCUMENTS

| | | |
|---|---|---|
| 6,295,944 B1 | 10/2001 | Lovett |
| 6,391,985 B1 | 5/2002 | Goode et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 7,244,150 B1 | 7/2007 | Brase et al. |
| 7,319,962 B2 | 1/2008 | Goedeke et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,688,235 B1 | 4/2014 | Pianca et al. |
| 8,706,251 B2 | 4/2014 | Von Arx et al. |
| 8,831,742 B2 | 9/2014 | Pianca et al. |
| 9,275,637 B1 | 3/2016 | Salvador et al. |
| 9,474,903 B2 | 10/2016 | Chen et al. |
| 9,561,380 B2 | 2/2017 | Carcieri et al. |
| 9,592,389 B2 | 3/2017 | Moffitt |
| 9,643,014 B2 | 5/2017 | Zhang et al. |
| 9,643,017 B2 | 5/2017 | Carcieri et al. |
| 9,781,086 B2 | 10/2017 | Jelatis et al. |
| 9,959,388 B2 | 5/2018 | Grandhe et al. |
| 10,071,249 B2 | 9/2018 | Zottola |
| 10,350,404 B2 | 7/2019 | Zhang et al. |
| 10,441,800 B2 | 10/2019 | Steinke |
| 10,603,498 B2 | 3/2020 | Blum et al. |
| 10,625,082 B2 | 4/2020 | Laghi |
| 10,716,505 B2 | 7/2020 | Blum et al. |
| 10,716,942 B2 | 7/2020 | Zhang |
| 10,744,330 B2 | 8/2020 | Moffitt et al. |
| 10,780,282 B2 | 9/2020 | Mustakos et al. |
| 2007/0043401 A1 | 2/2007 | John |
| 2007/0067004 A1 | 3/2007 | Boveja et al. |
| 2007/0150036 A1 | 6/2007 | Anderson |
| 2009/0187222 A1 | 7/2009 | Barker |
| 2009/0276021 A1 | 11/2009 | Meadows et al. |
| 2010/0023090 A1 | 1/2010 | Jaax et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0203366 A1 | 8/2012 | Saliger et al. |
| 2012/0316615 A1 | 12/2012 | DiGiore et al. |
| 2013/0105071 A1 | 5/2013 | DiGiore et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0353001 A1 | 12/2014 | Romero et al. |
| 2014/0353501 A1 | 12/2014 | Fantone et al. |
| 2014/0358024 A1 | 12/2014 | Nelson et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066110 A1* | 3/2015 | Tahmasian ......... A61N 1/36542 607/59 |
| 2015/0066120 A1 | 3/2015 | Govea |
| 2015/0151113 A1 | 6/2015 | Govea et al. |
| 2015/0182751 A1* | 7/2015 | Ghosh ................... A61N 1/371 607/28 |
| 2015/0306391 A1 | 10/2015 | Wu et al. |
| 2015/0348554 A1 | 12/2015 | Orr et al. |
| 2017/0223540 A1* | 8/2017 | Battiwalla ........... H04W 12/041 |
| 2017/0225007 A1 | 8/2017 | Orinski |
| 2017/0259078 A1 | 9/2017 | Howard |
| 2018/0110971 A1 | 4/2018 | Serrano Carmona |
| 2018/0369606 A1 | 12/2018 | Zhang et al. |
| 2018/0369607 A1 | 12/2018 | Zhang et al. |
| 2019/0036886 A1 | 1/2019 | Wu et al. |
| 2019/0156818 A1 | 5/2019 | Piersol et al. |
| 2019/0209834 A1 | 7/2019 | Zhang et al. |
| 2019/0209849 A1 | 7/2019 | Hershey et al. |
| 2020/0094047 A1 | 3/2020 | Govea et al. |
| 2020/0139140 A1 | 5/2020 | Crawford |
| 2020/0139141 A1* | 5/2020 | Crawford ................ H04L 67/34 |
| 2020/0155854 A1 | 5/2020 | Leven et al. |
| 2020/0252436 A1* | 8/2020 | Yoon ................. H04W 52/0229 |
| 2020/0305716 A1 | 10/2020 | Mondello et al. |
| 2020/0376262 A1 | 12/2020 | Clark et al. |

OTHER PUBLICATIONS

International Search Report and Written Opinion for PCT Application No. PCT/US2021/057018 mailed Apr. 26, 2022.

U.S. Appl. No. 63/112,537, filed Nov. 11, 2020.

* cited by examiner

# METHODS AND SYSTEMS FOR MANAGING ACCESS TO IMPLANTABLE MEDICAL DEVICES

CROSS-REFERENCE TO RELATED APPLICATIONS

This application claims the benefit under 35 U.S.C. § 119(e) of U.S. Provisional Patent Application Ser. No. 63/109,749, filed Nov. 4, 2020, which is incorporated herein by reference.

FIELD

The present disclosure is directed to the area of methods and systems for managing access to implantable medical devices from external devices. The present disclosure is also directed to methods and systems for managing access to implantable medical devices using authentication credentials.

BACKGROUND

Implantable electrical stimulation systems have proven therapeutic in a variety of diseases and disorders. For example, deep brain stimulation systems have been used as a therapeutic modality for the treatment of Parkinson's disease, essential tremor, and the like.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator in the IPG generates electrical pulses that are delivered by the electrodes to body tissue.

Implantable medical devices (IMDs), including IPGs, typically have the capability to communicate data with an external device, such as a clinician programmer or a remote control, via a radio-frequency telemetry link or other wireless communication method. The clinician programmer can program the operating parameters of the implanted medical device. The remote control can switch programs. Modern implantable devices also include the capability for bidirectional communication so that information can be transmitted to the clinician programmer or remote control from the implanted device.

BRIEF SUMMARY

One aspect is an external device for wireless communication with an implantable medical device. The external device includes a memory having stored thereon instructions for a first application configured to interact with implantable medical devices and authentication credentials specific to the first application; and a processor coupled to the memory and configured to perform actions including: executing the first application using the instructions; and transmitting the authentication credentials specific to the first application to an implantable medical device for the implantable medical device to authorize access to the implantable medical device by the first application.

In at least some aspects, the memory further has stored thereon instructions for a second application configured to interact with implantable medical devices and authentication credentials specific to the second application. In at least some aspects, the authentication credentials specific to the first application include identification of at least one specific implantable medical device or at least one specific type of implantable medical device that the first application is configured to interact with.

In at least some aspects, the authentication credentials specific to the first application include an end-entity certificate. In at least some aspects, the end-entity certificate includes an identification of the first application in custom metadata or certificate extensions of the end-entity certificate.

In at least some aspects, the authentication credentials specific to the first application include identification of at least one interaction capability of the first application with respect to an implantable medical device. In at least some aspects, at least one of the at least one interaction capability is selected from read data, write data, select from existing programs, modify programming settings of existing programs, create programs, modify or update software/firmware, or full control. In at least some aspects, the authentication credentials specific to the first application include an end-entity certificate and the end-entity certificate includes the identification of the at least one interaction capability in custom metadata or certificate extensions of the end-entity certificate.

Another aspect is a system that includes any of the external devices described above and an implantable medical device configured for wireless communication with the external device.

In at least some aspects, the authentication credentials specific to the first application include identification of the implantable medical device in the authentication credentials. In at least some aspects, the authentication credentials specific to the first application include identification of at least one interaction capability of the first application with respect to an implantable medical device and the implantable medical device is configured to limit authorized access to the implantable medical device by the first application to only the at least one interaction capability identified in the authentication credentials.

Yet another aspect is an external device for wireless communication with an implantable medical device. The external device includes a memory including authentication credentials stored thereon; and a processor coupled to the memory and configured to perform actions including: transmitting the authentication credentials to an implantable medical device for the implantable medical device to authorize access to the implantable medical device by the external device; receiving a request to facilitate authorization of the second device by the implantable medical device and receiving second authentication credentials from the second device; determining authentication or authorization of the second device using the second authentication credentials; and after authorization of the external device by the implantable medical device and determining authentication or authorization of the second device, transmitting a token or authorization credentials to at least one of the implantable medical device or the second device directing the implantable medical device to authorize access to the implantable medical device by the second device.

In at least some aspects, the token or authorization credentials are limited to a specified time period. In at least some aspects, the token or authorization credentials are limited to a single session.

A further aspect is a system that includes any of the external devices described in the preceding two paragraphs and a second device including a memory having stored thereon instructions for a second application configured to interact with implantable medical devices and the second authentication credentials, and a processor coupled to the memory and configured to perform actions including: executing the second application using the instructions; and transmitting the second authentication credentials specific to the external device.

In at least some aspects, the memory of the external device has further stored thereon instructions for a first application configured to interact with implantable medical devices, wherein the authentication credentials are specific to the first application and identify of at least one interaction capability of the first application with respect to an implantable medical device, and wherein the second authentication credentials identify of at least one interaction capability of the second application with respect to an implantable medical device.

In at least some aspects, the token or authorization credentials identify the at least one interaction capability of the first application. In at least some aspects, the token or authorization credentials identify the at least one interaction capability of the second application.

In at least some aspects, the system further includes the implantable medical device configured for wireless communication with the external device and the second device. In at least some aspects, the implantable medical device is configured to limit authorized access to the second device based on identification of at least one interaction capability in the token or authorization credentials.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of methods and systems for managing access to implantable medical devices from external devices. The present disclosure is also directed to methods and systems for managing access to implantable medical devices using authentication credentials.

The systems and methods described herein can be used with any suitable implantable medical devices. Implantable electrical stimulation systems and devices are used herein to exemplify the inventions, but it will be understood that these inventions can be utilized with other implantable medical devices. Examples of implantable electrical stimulation systems include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734;7, 761,165; 7,783,359; 7,792,590; 7,809,446; 7,949,395; 7,974,706; 8,831,742; 8,688,235; 8,175,710; 8,224,450; 8,271,094; 8,295,944; 8,364,278; and 8,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 1:
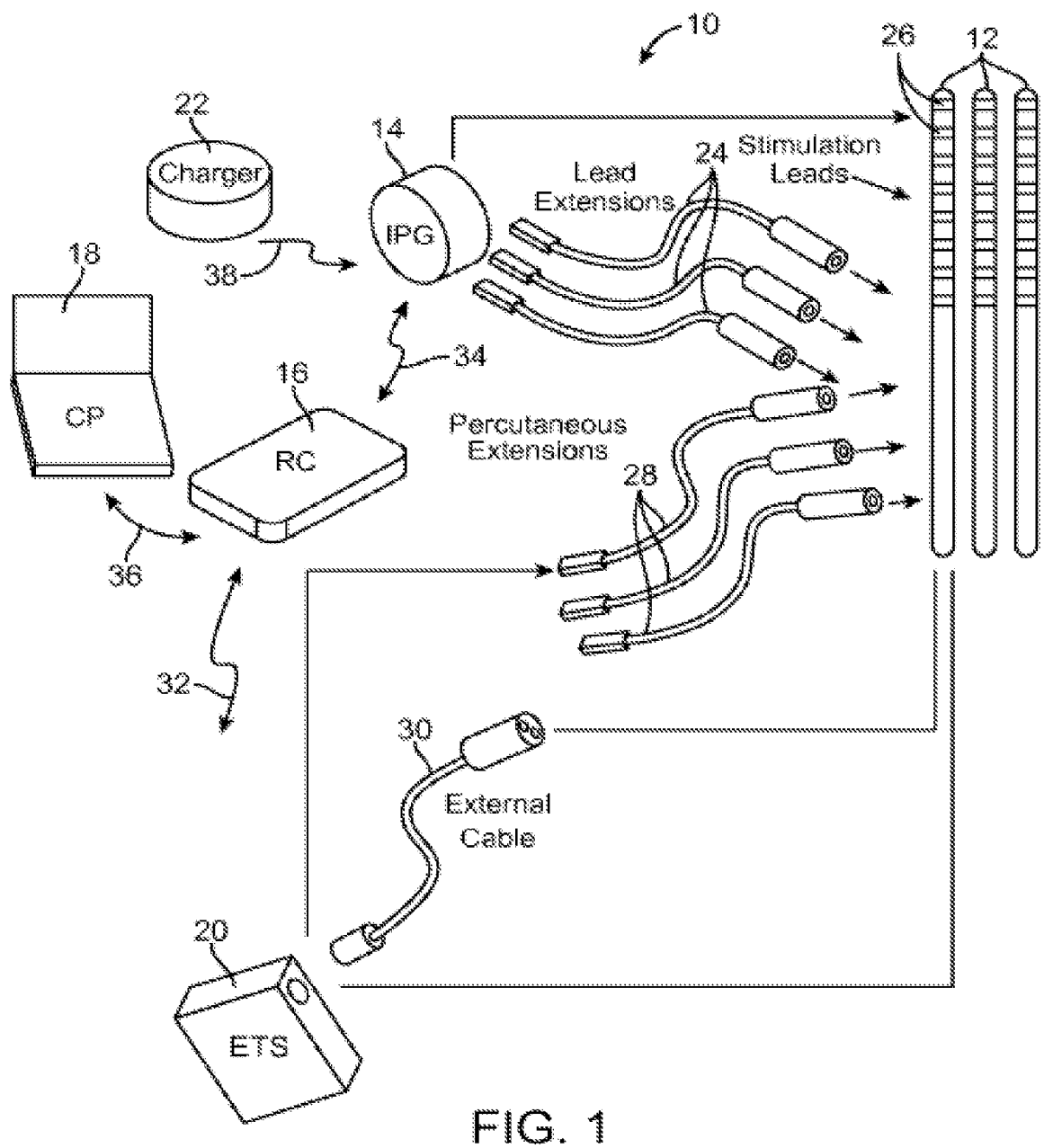
FIG. 1 is a schematic view of one embodiment of an electrical stimulation system that includes one or more leads that can be coupled to an IPG.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's abdominal cavity or at any other suitable site. The implantable pulse generator 14 can have multiple stimulation channels which may be independently programmable to control the magnitude of the current stimulus from each channel. In some embodiments, the implantable pulse generator 14 can have any suitable number of stimulation channels including, but not limited to, 4, 6, 8, 12, 16, 32, or more stimulation channels. The implantable pulse generator 14 can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14, for example, to be turned on or off and to be programmed with different stimulation parameter sets. The IPG 14 may also be operated to modify the programmed stimulation parameters to actively control the characteristics of the electrical stimulation energy output by the IPG 14. In at least some embodiments, the CP 18 allows a user, such as a clinician, the ability to program stimulation parameters for the IPG 14 and ETS 20 in the operating room and in follow-up sessions. Alternately, or additionally, in at least some embodiments, stimulation parameters can be programed via wireless communications (e.g., Bluetooth) between the RC 16 (or external device such as a hand-held electronic device like a mobile phone, tablet, or the like) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

Additional examples of the RC 16, CP 18, ETS 20, and external charger 22 can be found in the references cited herein as well as U.S. Pat. Nos. 6,895,280; 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, all of which are incorporated herein by reference in their entireties.

Figure 2:
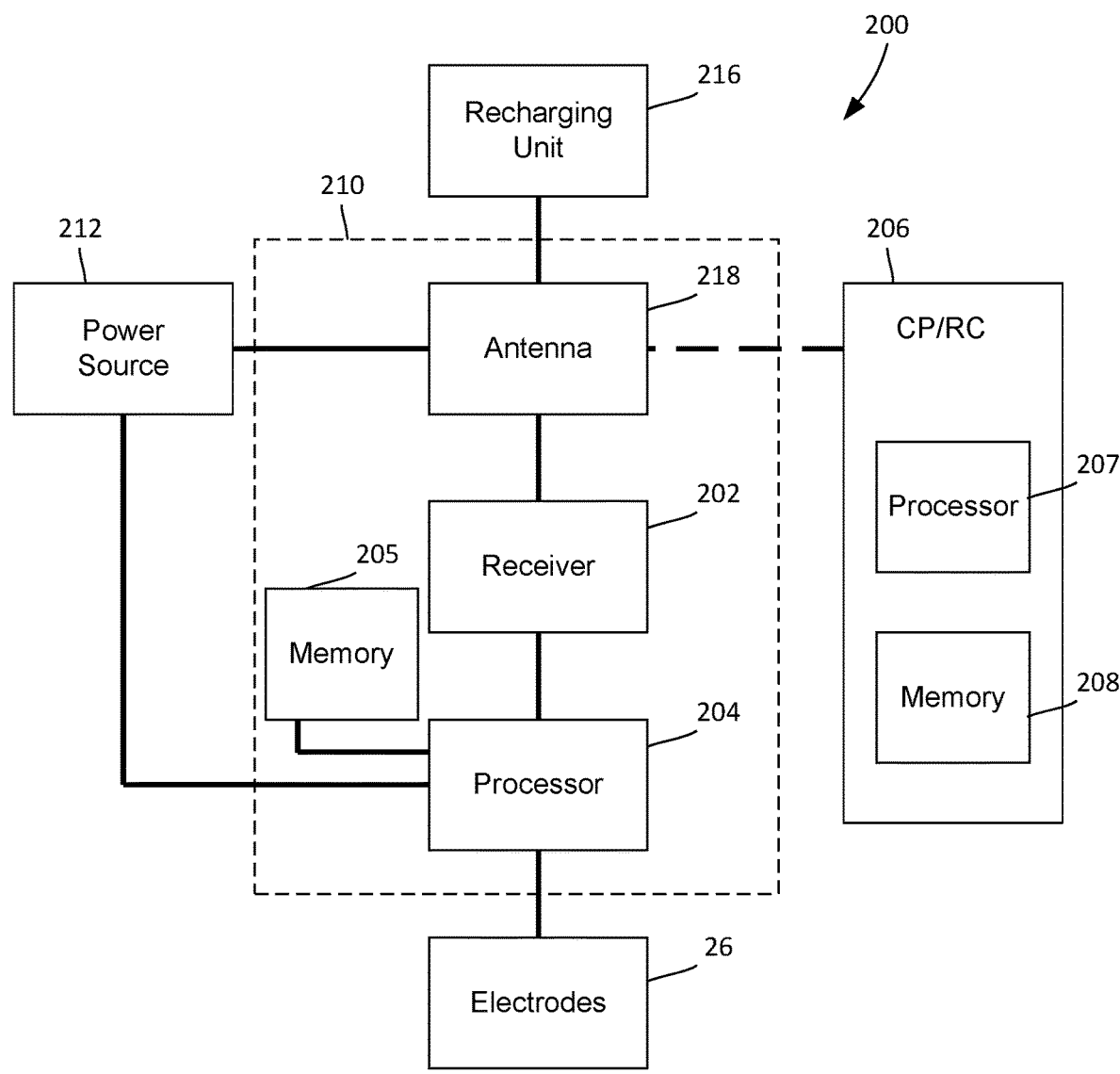
FIG. 2 is a block diagram of element of an electrical stimulation system.

FIG. 2 is a schematic overview of one embodiment of components of an electrical stimulation system 200 including an electronic subassembly 210 disposed within an IPG 14 (FIG. 1). It will be understood that the electrical stimulation system can include more, fewer, or different components and can have a variety of different configurations including those configurations disclosed in the stimulator references cited herein.

The IPG 14 (FIG. 1) can include, for example, a power source 212, antenna 218, receiver 202, processor 204, and memory 205. An external device, such as a CP or RC 206, can include a processor 207 and memory 208. Some of the components (for example, power source 212, antenna 218, receiver 202, processor 204, and memory 205) of the electrical stimulation system can be positioned on one or more circuit boards or similar carriers within a sealed housing of the IPG 14 (FIG. 1), if desired. Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 218 or a secondary antenna. The external power source can be in a device that is mounted on the skin of the user or in a unit that is provided near the user on a permanent or periodic basis.

If the power source 212 is a rechargeable battery, the battery may be recharged using the optional antenna 218, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 26 on the lead body to stimulate nerve fibers, muscle fibers, or other body tissues near the electrical stimulation system. A processor 204 is generally included to control the timing and electrical characteristics of the electrical stimulation system. For example, the processor 204 can, if desired, control one or more of the timing, frequency, amplitude, width, and waveform of the pulses. In addition, the processor 204 can select which electrodes can be used to provide stimulation, if desired. In some embodiments, the processor 204 may select which electrode(s) are cathodes and which electrode(s) are anodes. In some embodiments, the processor 204 may be used to identify which electrodes provide the most useful stimulation of the desired tissue. Instructions for the processor 204 can be stored on the memory 205. Instructions for the processor 207 can be stored on the memory 208.

Any processor 204 can be used for the IPG and can be as simple as an electronic device that, for example, produces pulses at a regular interval or the processor can be capable of receiving and interpreting instructions from the CP/RC 206 (such as CP 18 or RC 16 of FIG. 1) that, for example, allows modification of pulse characteristics. In the illustrated embodiment, the processor 204 is coupled to a receiver 202 which, in turn, is coupled to the optional antenna 218. This allows the processor 204 to receive instructions from an external source to, for example, direct the pulse characteristics and the selection of electrodes, if desired. Any suitable processor 207 can be used for the CP/RC 206.

Any suitable memory 205, 208 can be used including computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include, but are not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a processor.

In one embodiment, the antenna 218 is capable of receiving signals (e.g., RF signals) from a CP/RC 206 (see, CP 18 or RC 16 of FIG. 1) which is programmed or otherwise operated by a user. The signals sent to the processor 204 via the antenna 218 and receiver 202 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 200 to cease operation, to start operation, to start charging the battery, or to stop charging the battery. In other embodiments, the stimulation system does not include an antenna 218 or receiver 202 and the processor 204 operates as programmed.

Optionally, the electrical stimulation system 200 may include a transmitter (not shown) coupled to the processor 204 and the antenna 218 for transmitting signals back to the CP/RC 206 or another unit capable of receiving the signals. For example, the electrical stimulation system 200 may transmit signals indicating whether the electrical stimulation system 200 is operating properly or not or indicating when the battery needs to be charged or the level of charge remaining in the battery. The processor 204 may also be capable of transmitting information about the pulse characteristics so that a user or clinician can determine or verify the characteristics.

Transmission of signals can occur using any suitable method, technique, or platform including, but not limited to, inductive transmission, radiofrequency transmission, Bluetooth™, Wi-Fi, cellular transmission, near field transmission, infrared transmission, or the like or any combination thereof. In addition, the IPG can be wirelessly coupled to the RC or CP using any suitable arrangement include direct transmission or transmission through a network, such as a local area network, wide area network, the Internet, or the like or any combination thereof.

Returning to FIG. 1, the CP 18 or RC 16 (or other external device) utilizes software applications to communicate with the IPG 14. These software applications are often custom-made and instructions for the software applications can be stored in the memory of the CP, RC, or other external device. In at least some embodiments, depending on its purpose, each software application may have a capability (or permission) to perform one or more of the following: read data, write data, select from existing programs, modify programming settings of existing programs, create programs, modify or update software/firmware, full control (which could include all of the previously listed capabilities), or otherwise interact with the IPG or any combination of these capabilities (or permissions).

It will also be understood that although the methods, techniques, and systems described herein are presented in the context of an external device, such as a CP or RC, communicating with an IPG, these methods, techniques, and systems can be used for communication and authentication of an external device with any medical device. In addition, the methods, techniques, and systems described herein are presented in the context of an electrical stimulation system, but it will be recognized that these methods, techniques, and systems can be used with an optical stimulation system or an electrical/optical stimulation system. Examples of optical stimulation systems or electrical/optical stimulation systems are found in U.S. Patent Application Publications Nos. 2013/0317572; 2013/0317573; 2017/0259078; 2017/0225007; 2018/0110971; 2018/0369606; 2018/0369607; 2019/0209849; 2019/0209834; 2020/0094047; and 2020/0155854 and U.S. patent application Ser. No. 16/883,404, all of which are incorporated herein by reference in their entireties.

The CP, RC, or other external device can use any suitable authentication mechanism, such as certificate or credential authentication, encrypted messaging, or both, to securely communicate with an IPG. In at least some embodiments, the authentication mechanism includes an external device (such as a CP or RC) transmitting authentication credentials, such as a digital certificate (for example, an end-entity certificate), to the IPG to authenticate the external device. The authentication credentials can be stored in the memory of the external device. Once authenticated by the IPG, the IPG authorizes access to the IPG by the external device. Examples of authentication credentials and authentication of an external device with a medical device are described in U.S. Pat. No. 9,781,086, which is incorporated herein by reference in its entirety. In at least some embodiments, the transmissions between the external device and the IPG are encrypted. Examples of encryption methods are described in U.S. Pat. No. 8,706,251, which is incorporated herein by reference in its entirety. Any other suitable encryption methods and techniques can be used including, but not limited to, public key encryption (e.g., RSA encryption) or AES encryption.

A certificate or other authentication credentials are typically issued and signed by a trusted authority, such as a certificate authority. The IPG (or other medical device) can compare the certificate or other authentication credentials received from the external device with a certificate or authentication credentials (which can be stored in the memory of the IPG) that the IPG has received from the trusted authority to authenticate the external device. In at least some embodiments, the authentication credentials issued to an external device can identify one or more specific IPGs (for example, by serial number or the like) or one or more specific types of IPGs (for example, by model or serial number range or the like or any combination thereof).

In at least some embodiments, the authentication and subsequent authorized access may be time-limited or session-limited. In at least some embodiments, after the time limit or session, the external device must be reauthenticated to be authorized access to the IPG. In at least some embodiments, authorized access to an IPG may also be limited by the number of connections, duration of connection, location, or the like or any combination thereof.

An end-entity certificate will be used herein as an example of authentication credentials. It will be understood, however, that any other suitable authentication credentials can be substituted for the end-entity certificate and those authentication credentials can include or be modified to include the elements described herein and be used according to the methods described herein.

In at least some embodiments, the end-entity certificate is organized according to the X.509 (e.g., the X.509 v3) certificate specification from the International Telecommunications Union (ITU). Any other suitable type of certificate or certificate specification can be used. The end-entity certificate can include information such as, for example, the specification and version of certificate (for example, an X.509 v3 certificate); the serial number of the certificate; the signature algorithm used to sign the certificate; the issuer name (for example, the name of the certificate authority that issued the certificate); a validity period for the certificate (for example, a start date/time and an end date/time); identifying information (for example, type, model, serial number, or the like or any combination thereof) regarding the end entity that is intended to receive the certificate (for example, the certificate subject); the public key algorithm and public key for the end entity; optional certificate extensions such as constraints, the type of certificate, certificate policies, or custom metadata that may be supplied by a manufacturer, supplier, or user of the external device or the end entity; the certificate signature algorithm; the certificate signature; or the like or any combination thereof. Other certificates can contain more or fewer elements of information.

In at least some embodiments, the end-entity certificate (or other authentication credentials) that is transmitted from the external device to a medical device, such as an IPG, is not specific to a particular application on the external device. An external device, however, may have multiple applications stored thereon. For example, the external device may have different applications so that the external device can interact with different types of IPGs. In at least some embodiments, only a subset (for example, only one or more, but less than all) of those applications are suitable for any particular type of IPG with which the external device is to communicate. For example, a CP or RC may include a first application that is suitable for use with a first type of IPG and a second application that is suitable for use with a second type of IPG. Such an arrangement can be useful so that the CP or RC is not limited to use with only a specific type or types of IPGs or other medical devices.

As another example, a CP or RC may include a first application that is suitable for use by a patient and a second application that is suitable for use by a clinician. These applications may require that the individual (e.g., patient or clinician) enter a password or other identification for access to the appropriate application(s). The first and second applications may have different capabilities. For example, the patient-accessible first application may allow the patient to select from a number of different stimulation programs, but not allow the patient to modify or create stimulation programs. In contrast, the clinician-accessible second application may permit modification or creation of stimulation programs. Such an arrangement may be useful as it can provide a single device with different capabilities for different users.

Because a particular CP or RC may have a number of different software applications, it can be useful to control which specific applications and devices are authorized to access specific IPGs. In at least some embodiments, application-specific end-entity certificates (or other application-specific authentication credentials) are individually (or collectively for a subset of applications) issued for one or more (or all) of the applications on an external device. In at least some embodiments, the application-specific end-entity certificate or (other application-specific authentication credentials) can securely communicate identity information about the application and the external device to the IPG in order to obtain authorized access to the IPG. For example, the end-entity certificate (or other authentication credentials) can contain information about the type(s) or identity(ies) of the IPGs that the application is authorized to communicate with or information about the application or type of application that is associated with the end-entity certificate (or other authentication credentials). In at least some embodiments, this information can be contained in the custom metadata or other optional certificate extensions of the end-entity certificate issued to that application and communicated to the IPG.

In at least some embodiments, the IPG authenticates and positively identifies the external device and the application (or application type) and determines whether the external device and application (or application type) are authorized access to, and communicate with, the IPG using the information provided in the end-entity certificate (or other authentication credentials). For example, the IPG may use the information regarding the type(s) or identity(ies) of the IPG the application is authorized to communicate with or information about the application or type of application to authorize access by the external device and by the application identified in the end-entity certificate (or other authentication credentials).

In at least some embodiments, the IPG terminates or prevents communication with an application or external device that is not authenticated and, therefore, not authorized to communicate and interact with that IPG. For example, if the IPG identified in the end-entity certificate (or other authentication credentials) does not match the IPG that receives the end-entity certificate (or other authentication credentials) then the IPG terminates or prevents communication with an application or external device or terminates or prevents access by the application or external device. As another example, if the application identified in the end-entity certificate (or other authentication credentials) does not match an application authorized on the IPG that receives the end-entity certificate (or other authentication credentials) then the IPG terminates or prevents communication with an application or external device or terminates or prevents access by the application or external device.

Figure 3:
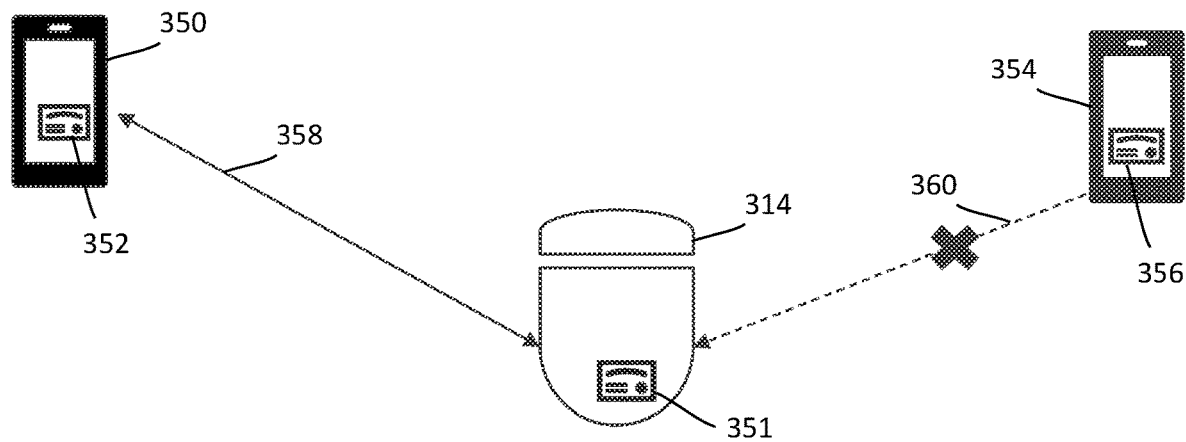
FIG. 3 is a schematic illustration of authentication between an IPG and two external devices.

FIG. 3 illustrates an IPG 314, a first external device 350 (such as a CP or RC), and a second external device 354 (such as a CP or RC). The first external device 350 has an application with an associated first end-entity certificate 352 (or other authentication credentials), which may be an application-specific end-entity certificate. The second external device 354 has an application with an associated second end-entity certificate 356 (or other authentication credentials), which may be an application-specific end-entity certificate.

In the illustrated embodiment, the first end-entity certificate 352 identifies the IPG 314 within the first end-entity certificate 352 and, therefore, the first external device 350 is authenticated by the IPG 314 using the IPG's certificate 351 and communication 358 continues between the IPG 314 and the first external device 350 because the first external device is authorized access to the IPG. In contrast, the second end-entity certificate 356 identifies a different IPG, not IPG 314, within the second end-entity certificate 356 and, therefore, the second external device 354 is not authenticated by the IPG 314 and communication 360 between the second external device 354 and IPG 314 or access to the IPG is terminated or not authorized.

Figure 4:
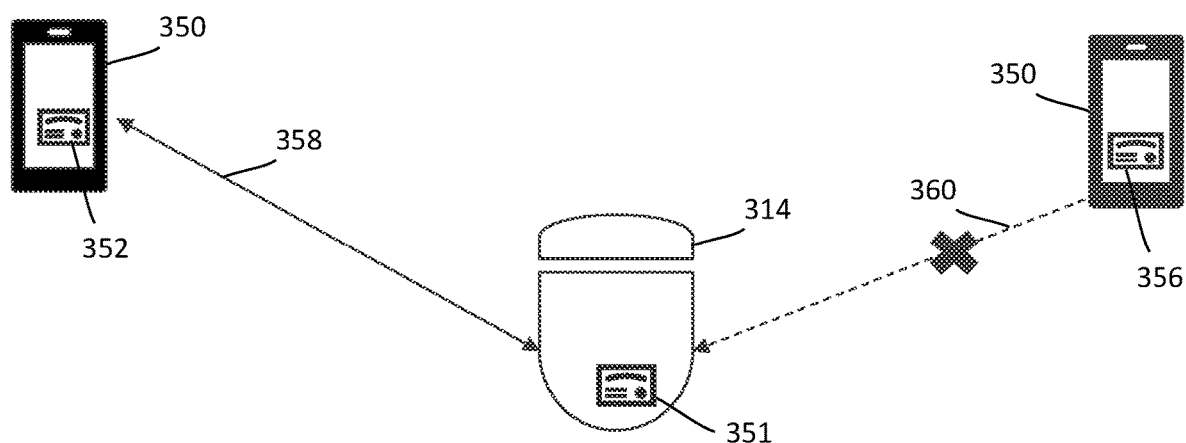
FIG. 4 is a schematic illustration of authentication between an IPG and two applications on an external device.

FIG. 4 illustrates an IPG 314 and an external device 350 with a first end-entity certificate 352 that is application-specific to a first application and a second end-entity certificate 356 that is application-specific to a second application. (The external device 350 is illustrated twice in FIG. 4 for ease of depiction.) In at least some embodiments, the first application-specific first end-entity certificate 352 identifies the IPG 314 and the first application within the first end-entity certificate 352 and, therefore, the application is authenticated by the IPG 314 using the IPG's certificate 351 and communication 358 continues between the IPG 314 and the first application because the first application is authorized access to the IPG. In contrast, the second application-specific second end-entity certificate 356 identifies a different IPG, not IPG 314, within the second end-entity certificate 356 and, therefore, the second application is not authenticated by the IPG 314 and communication 360 between the second application and IPG 314 is terminated or not authorized.

In other embodiments, in FIG. 4, the IPG 314 identifies the first application as authorized to interact with the IPG and, therefore, the application is authenticated by the IPG 314 using the IPG's certificate 351 and communication 358 continues between the IPG 314 and the first application because the first application is authorized access to the IPG. In contrast, the IPG 314 recognizes that the second application is not authorized to interact with the IPG and, therefore, the second application is not authenticated by the IPG 314 and communication 360 between the second application and IPG 314 is terminated or not authorized.

Figure 5:
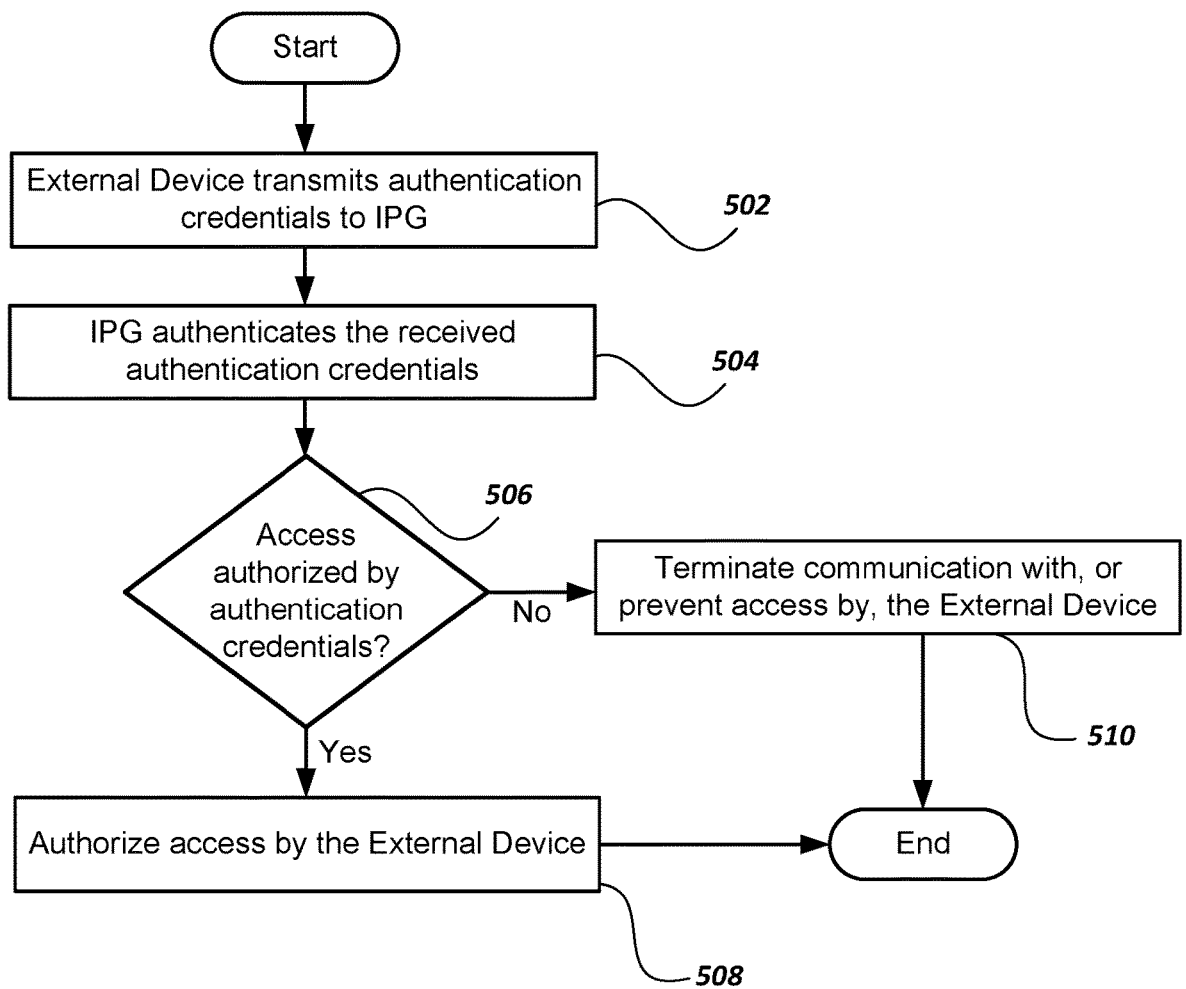
FIG. 5 is a flowchart of one embodiment of method of authorizing access to an IPG by an external device.

FIG. 5 is a flowchart of one embodiment of a method of authorizing access to an IPG (or other medical device) by an external device (such as a RC or CP). In step 502, the external device transmits authentication credentials (such as an end-entity certificate) to the IPG (or other medical device). In at least some embodiments, the authentication credentials can be application-specific. In step 504, the IPG (or other medical device) authenticates the received authentication credentials. In step 506, the IPG (or other medical device) determines from the received authentication credentials whether access by the external device or application of the external device is authorized. If yes, in step 508, access by the external device or application of the external device is authorized. If no, in step 510, communication with the external device is terminated or access by the external device or application of the external device is prevented.

In at least some embodiments, an external device can include more than one application that can connect to the IPG. In at least some embodiments, the application(s) each have one or more interaction capabilities with respect to the IPG and those interaction capabilities can differ between applications. The term "permission" can be used interchangeably with the term "capability". Examples of interaction capabilities include, but are not limited to, read data, write data, select from existing programs, modify programming settings of existing programs, create programs, modify or update software/firmware, full control (which could include all of the previously listed capabilities), or the like or any combination thereof.

As one example, one application may be authorized for only read capability and another application may be authorized for full control capability. As a further example, a RC or CP could include i) a patient application that has, for example, read and program selection capabilities; ii) a clinician application which has, for example, read, write, program selection, modifying programming settings of existing programs, and creating programs (or even has full control); and iii) a manufacturer application that has, for example, full control or read, write, and software/firmware update capabilities. Other applications, including other patient, clinician, or manufacturer applications, can have different interaction capabilities or sets of interaction capabilities.

Each application is limited to only the interaction capabilities authorized for that application. Examples of other interaction capabilities or interaction capability restrictions can include, for example, security-based limitations, clinician-controlled settings, and remote therapy adjustment.

In at least some embodiments, an application-specific end-entity certificate (or other application-specific authentication credentials) can include interaction capability information about the application. For example, information about the application's interaction capabilities can be contained in the custom metadata or other certificate extensions of the end-entity certificate issued to that application and communicated to the IPG. In at least some embodiments, the interaction capabilities in the application-specific end-entity certificate (or other application-specific authentication credentials) include all of the interaction capabilities that the application is capable of. In at least some embodiments, the interaction capabilities may be determined by (or in view of) or limited by (or in view of) the signing entity (e.g., certificate authority or a sub-certificate authority) of the end-entity certificate (or other authentication credentials).

In other embodiments, the interaction capabilities in the application-specific end-entity certificate (or other application-specific authentication credentials) may not include all of the interaction capabilities that the application is capable of, but only a subset of those capabilities. For example, an application may be useable by both a patient and a clinician, but the application on the patient's RC may have an end-entity certificate (or other application-specific authentication credentials) that only includes, for example, read and program selection capabilities. The application on a clinician's CP may have an end-entity certificate (or other application-specific authentication credentials) that includes, for example, read, write, program selection, modifying programming settings of existing programs, and creating programs (or even includes full control).

Alternatively, in at least some embodiments, an end-entity certificate (or other authentication credentials) for an external device may specify interaction capabilities for all applications of that external device. For example, an RC may have an end-entity certificate (or other application-specific authentication credentials) that only has, for example, read and program selection capabilities. A CP may have an end-entity certificate (or other application-specific authentication credentials) that has, for example, read, write, program selection, modifying programming settings of existing programs, and creating programs (or even has full control).

In at least some embodiments, the IPG authenticates or validates the application capabilities using the end-entity certificate (or other authentication credentials). In at least some embodiments, the IPG authenticates or validates the application's interaction capabilities by identifying the capabilities listed within the custom metadata or other certificate extensions of an application-specific end entity certificate.

In at least some embodiments, the IPG only allows or authorizes access to the IPG based on the interaction capabilities listed for the application or external device in the end entity certificate (or other credentials). For example, if the application's interaction capabilities in the end-entity certificate (or other authentication credentials) only allow read access, the IPG prevents write operations.

Figure 6:
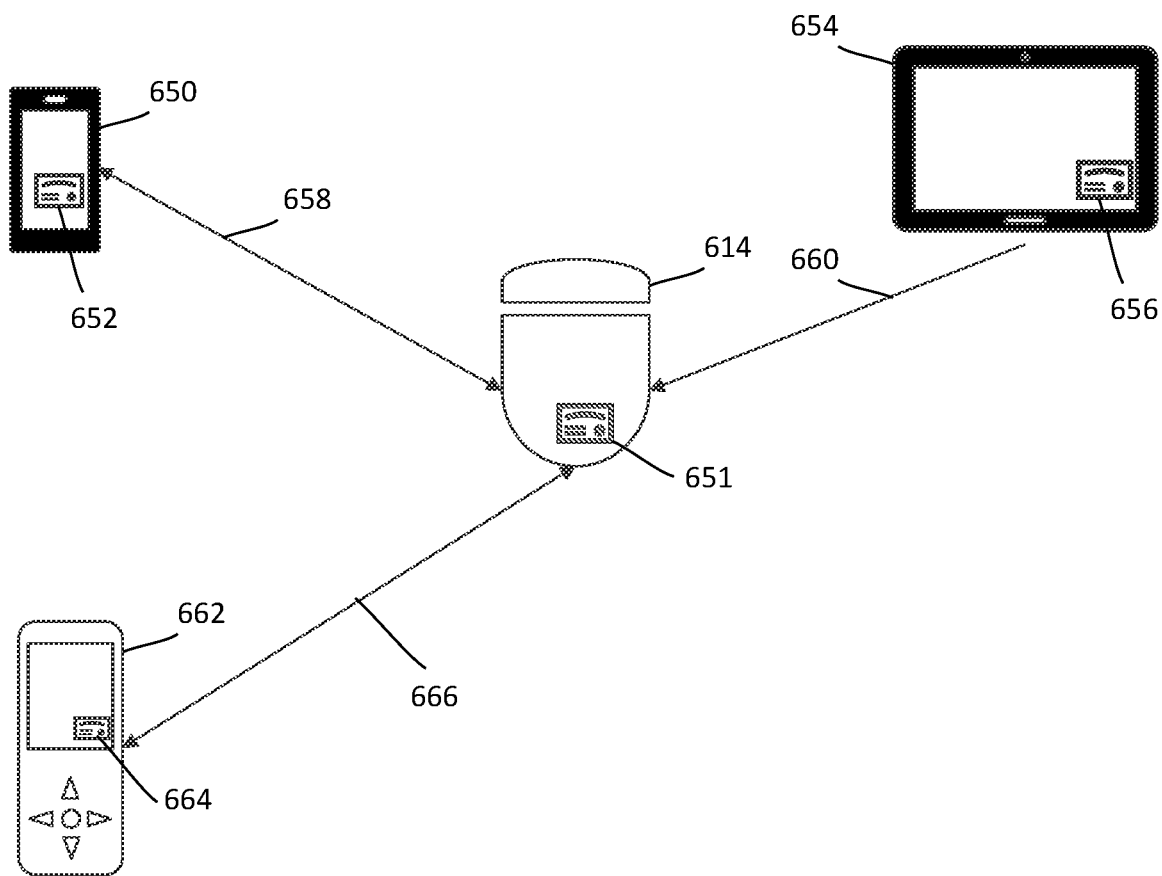
FIG. 6 is a schematic illustration of authentication between an IPG and external devices or applications of an external device and also indicating interaction capabilities of the external devices or applications.

FIG. 6 illustrates an IPG 614, a first external device 650 (such as a RC), a second external device 654 (such as a CP), and a third external device 662 (such as a second RC). The first external device 650 has an application with an associated application-specific first end-entity certificate 652 (or other authentication credentials). The second external device 654 has a second end-entity certificate 656 (or other authentication credentials) for the second external device. The third external device 662 has a third end-entity certificate 652 (or other authentication credentials) for the third external device.

In the illustrated embodiment, the application-specific first end-entity certificate 652 identifies the IPG 614 within the first end-entity certificate 652 and indicates that the application has only read capability. Therefore, the application of the first external device 650 is authenticated by the IPG 614 using the IPG's certificate 651 and communication 658 continues between the IPG 614 and the application of the first external device 650 because the application of the first external device is authorized access to the IPG. The application of the first external device 650, however, has only the read capability.

The second end-entity certificate 656 identifies the IPG 614 within the second end-entity certificate 656 and indicates that the second external device 654 has full control capability. Therefore, the second external device 654 is authenticated by the IPG 614 using the IPG's certificate 651 and communication 660 continues between the IPG 614 and the second external device 654 because the second external device is authorized access to the IPG. The applications of the second external device 654 have full control capability.

The third end-entity certificate 664 identifies the IPG 614 within the second end-entity certificate 664 and indicates that the third external device 664 has read, write, modify programming settings of existing programs, and create programs capabilities. Therefore, the third external device 664 is authenticated by the IPG 614 using the IPG's certificate 651 and communication 666 continues between the IPG 614 and the third external device 664 because the third external device is authorized access to the IPG. The applications of the third external device 654 have read, write, modify programming settings of existing programs, and create programs capabilities.

Figure 7:
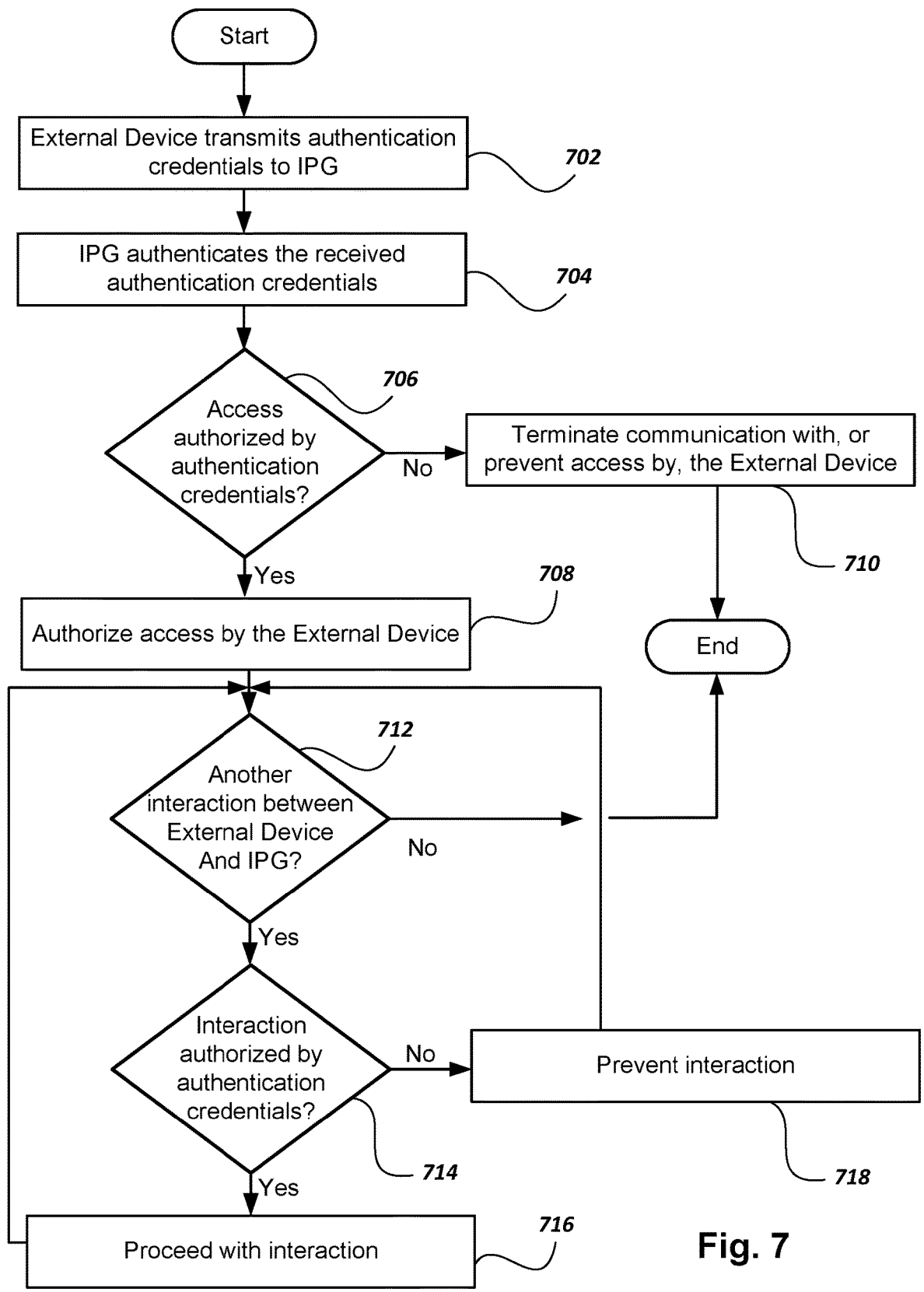
FIG. 7 is a flowchart of one embodiment of method of authorizing access to an IPG by an external device and authorizing interaction capabilities by the external device or an application on the external device.

FIG. 7 is a flowchart of one embodiment of a method of authorizing access to an IPG (or other medical device) by an external device. In step 702, the external device transmits authentication credentials (such as an end-entity certificate) to the IPG (or other medical device). The authentication credentials include an indication of one or more interaction capabilities of the external device or one or more applications of the external device. In at least some embodiments, the authentication credentials can be application-specific. In step 704, the IPG (or other medical device) authenticates the received authentication credentials. In step 706, the IPG (or other medical device) determines from the received authentication credentials whether access by the external device or application of the external device is authorized. If yes, in step 708, access by the external device or application of the external device is authorized. If no, in step 710, communication with the external device is terminated or access by the external device or application of the external device is prevented.

In step 712, there is a determination whether the external device (or an application of the external device) is interacting with the IPG. If so, in step 714, the IPG determines whether the interaction falls within the interaction capabilities specified in the authentication credentials. If so, in step 716, the IPG and external device proceed with the interaction. If not, in step 718, the IPG prevents the interaction.

In some embodiments, an authorized first external device can facilitate the authentication or authorization of a second external device. For example, a RC that is authorized, using authentication credentials as described above, to access an IPG can facilitate the authentication or authorization of a CP to provide authorized access to the IPG by the CP. This can be particularly useful when, for example, the RC (which is intended to communicate with a specific IPG) has authorization credentials that specify the IPG but the CP (which is intended to communicate with any suitable IPG) does not.

In at least some embodiments, the first external device can present authentication credentials to the IPG (or other medical device) and thereby obtain authorized access to the IPG, as described above. The second external service presents authentication credentials to the first external device which confirms the authentication credentials. For example, the first external device can compare the authentication credentials from the second external device to the authentication credentials (e.g., a certificate from a trusted authority) on the first external device. After verification, the first external device provides a token or other authorization credentials to either the IPG or the second external device that authorizes access to the IPG by the second external device.

Figure 8:
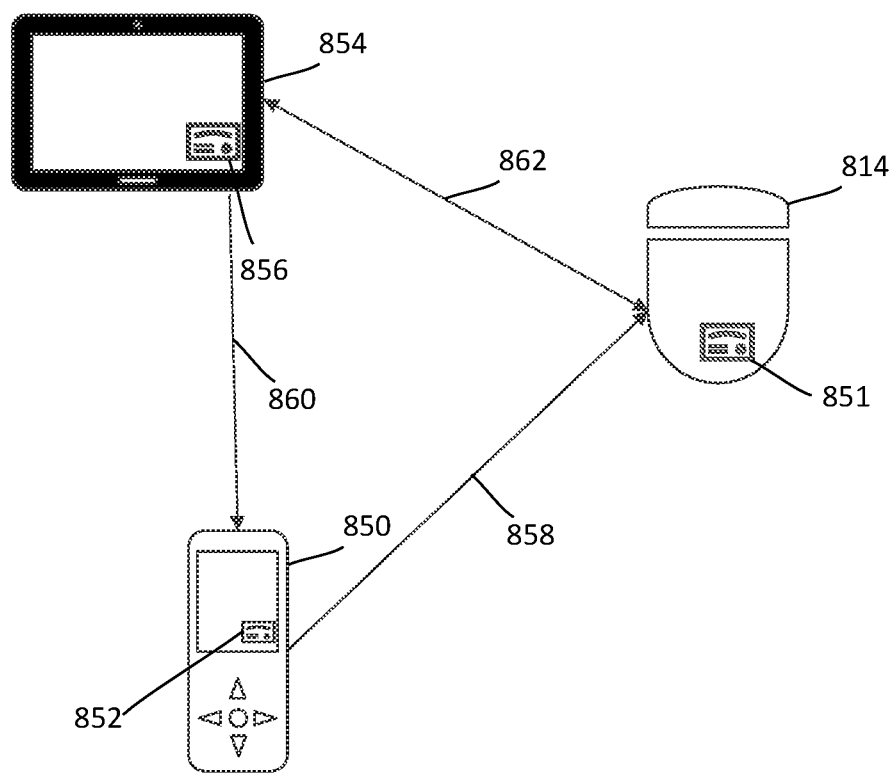
FIG. 8 is a schematic illustration of access authorization to an IPG by a second external device using an authorized first external device to authenticate the second external device.

FIG. 8 illustrates an IPG 814, a first external device 850 (such as a RC), and a second external device 854 (such as a CP). The first external device 850 has first authentication credentials 852 (such as a first end-entity certificate), which may be application-specific authentication credentials. The second external device 854 has second authentication credentials 856, which may be application-specific authentication credentials.

In the illustrated embodiment, the first authentication credentials 852 identifies the IPG 814 within the first authentication credentials 852 and, therefore, the first external device 850 is authenticated by the IPG 814 using the IPG's certificate 851 and communication 858 continues between the IPG 814 and the first external device 850 because the first external device is authorized access to the IPG.

The second external device 854 does not have authentication credentials that specify IPG 314 and so the second external device cannot directly authenticate with the IPG. The second external device 854 communicates 860 with the first external device 850 and presents the second authentication credentials 856 to the first external device. The first external device 850 authenticates the second external device 854 using the second authentication credentials 856 and authorizes access to the IPG 314 which may be based on the authorized access that the first external device has obtained using its own first authentication credentials 852. The first external device 850 provides either the second external device 854 or the IPG 314 with a token or other authorization credentials so that the second external device can communicate 862 with, and have authorized access to, the IPG 314.

In some embodiments, interaction capabilities, as described above, may be specified in one or both of the first authentication credentials 852 or the second authentication credentials 856. In at least some embodiments, the first external device 850 can authorize any interaction capabilities specified in the second authentication credentials 856. In at least some embodiments, the first external device 850 can authorize only those interaction capabilities specified in the first authentication credentials 852.

Figure 9:
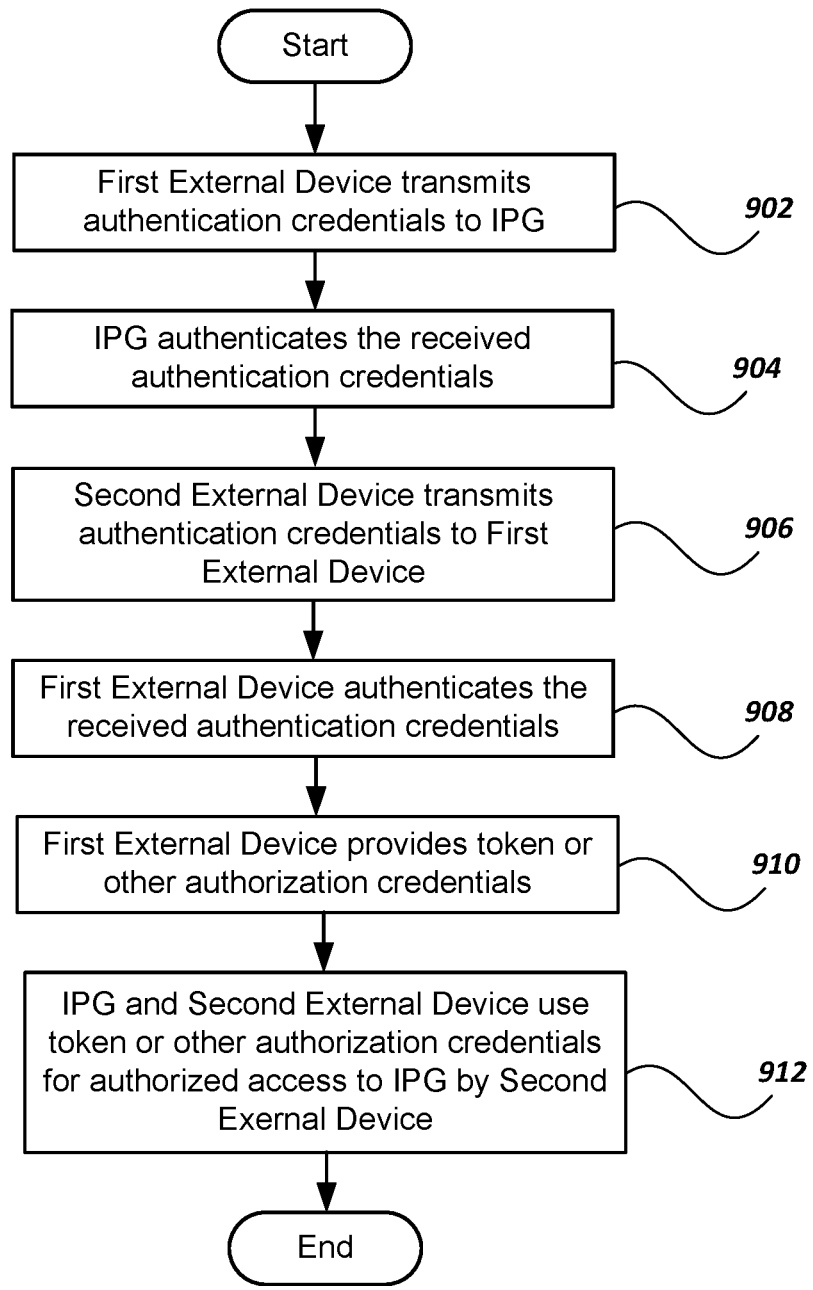
FIG. 9 is a flowchart of one embodiment of method of authorizing access to an IPG by a second external device using an authorized first external device to authenticate the second external device.

FIG. 9 is a flowchart of one embodiment of a method of authorizing access to an IPG (or other medical device) using a first external device to authorize access by a second external device. In step 902, the first external device transmits authentication credentials (such as an end-entity certificate) to the IPG (or other medical device). In at least some embodiments, the authentication credentials can be application-specific. In step 904, the IPG (or other medical device) authenticates the received authentication credentials to authorize access by the first external device (see, for example, the methods described above). In step 906, the second external device transmits authentication credential to the first external device. In step 908, the first external device authenticates the received authentication credentials from the second external device to authorize access to the IPG by the second external device. In step 910, the first external device provides a token or other authorization credentials to the second external device or IPG or both. In step 912, the IPG and second external device use the token or other authorization credentials for authorized access to the IPG by the second external device.

In at least some embodiments, the token or other authorization credentials can be limited by time or limited to a session or by any other suitable limitation(s). Such limitation(s) may be imposed by the first external device, IPG, or second external device or any combination thereof.

Any of the systems or methods described herein may also incorporate two-factor authentication. For example, the systems or methods may also require that the user provide identification to the external device, such as a password, fingerprint, or code that has been sent to another user device, or the like or any combination thereof. In at least some embodiments, the IPG may require two-factor authentication by entry of a password or by application of a magnet near the IPG. For example, a specified sequence of on-off steps may be required by the IPG for the second authentication factor where "on" indicates that the magnet is near the IPG and "off" indicates that the magnet has been removed from proximity to the IPG. One example of such a sequence can be "on"-"off"-"on".

In at least some embodiments, a patient may provide a fingerprint, password, or other identification to register a first external device (such as a RC) to the patient. The first external device can provide the fingerprint, password, or other identification to the IPG. Subsequently, each second external device that is to be authenticated with the IPG will also provide the fingerprint, password, or other identification along with other authentication credentials to demonstrate that the patient has given consent to access to the IPG. In at least some embodiments, the patient may request that the first external device provide the fingerprint, password, or other identification to the second external device. Such a request may require that the patient provide or enter the fingerprint, password, or other identification into the first external device.

It will be understood that each block of the flowchart illustration, and combinations of blocks in the flowchart illustration and methods disclosed herein, can be implemented by computer program instructions. These program instructions may be provided to a processor to produce a machine or engine, such that the instructions, which execute on the processor, create means for implementing the actions specified in the flowchart block or blocks or engine disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. The computer program instructions can be stored locally or nonlocally (for example, in the Cloud).

The above specification and examples provide a description of the arrangement and use of the invention. Since many embodiments of the invention can be made without departing from the spirit and scope of the invention, the invention also resides in the claims hereinafter appended.

What is claimed as new and desired to be protected is:

1. An external device for wireless communication with an implantable medical device, the external device comprising:
a memory comprising first authentication credentials stored thereon; and
a processor coupled to the memory and configured to perform actions comprising:
transmitting the first authentication credentials directly to the implantable medical device for the implantable medical device to authorize access to the implantable medical device by the external device, wherein the first authentication credentials comprise a first certificate issued to the external device by a certificate authority, wherein the first certificate identifies the external device;
receiving a request to facilitate authorization of a second device by the implantable medical device and receiving second authentication credentials from the second device, wherein the second authentication credentials comprise a second certificate issued to the second device by a certificate authority, wherein the second certificate identifies the second device;
determining authentication or authorization of the second device using the second authentication credentials; and
after authorization of the external device by the implantable medical device and determining authentication or authorization of the second device, transmitting a token or third authorization credentials to at least one of the implantable medical device or the second device directing the implantable medical device to authorize direct access to the implantable medical device by the second device so that both the external device and the second device have authorized direct access to the implantable medical device.

2. The external device of claim 1, wherein the memory has further stored thereon instructions for a first application configured to interact with implantable medical devices, wherein the first certificate comprises explicit identification of at least one interaction capability of the first application with respect to the implantable medical device, wherein each of the at least one interaction capability identifies a specific interaction with the implantable medical device, wherein at least one of the at least one interaction capability is selected from i) selecting from existing stimulation programs, ii) modifying programming settings of existing stimulation programs, or iii) creating stimulation programs;
wherein the actions further comprise:
executing the first application using the instructions; and
transmitting the first authentication credentials to the implantable medical device for the implantable medical device to authorize access to the implantable medical device by the first application limiting interaction between the first application and the implantable medical device to the at least one interaction capability explicitly identified in the first certificate.

3. The external device of claim 2, wherein the memory further has stored thereon instructions for a second application configured to interact with implantable medical devices and additional authentication credentials specific to the second application.

4. The external device of claim 2, wherein the first authentication credentials comprise identification of at least one specific implantable medical device or at least one specific type of implantable medical device that the first application is configured to interact with.

5. The external device of claim 2, wherein the first certificate comprises an end-entity certificate.

6. The external device of claim 5, wherein the end-entity certificate comprises an identification of the first application in custom metadata or certificate extensions of the end-entity certificate.

7. The external device of claim 2, wherein the at least one interaction capability is at least two interaction capabilities, wherein at least another one of the at least two interaction capabilities is selected from reading data, writing data, or modifying or updating software/firmware.

8. A system, comprising:
the external device of claim 2; and
the implantable medical device configured for wireless communication with the external device.

9. The system of claim 8, wherein the first authentication credentials comprise identification of the implantable medical device in the first authentication credentials.

10. The system of claim 8, wherein the implantable medical device is configured to limit authorized access to the implantable medical device by the first application to only the at least one interaction capability identified in the first authentication credentials.

11. The external device of claim 1, wherein the token or third authorization credentials are limited to a specified time period.

12. The external device of claim 1 wherein the token or third authorization credentials are limited to a single session.

13. A system, comprising:
the external device of claim 1; and
the second device comprising
a memory having stored thereon instructions for a second application configured to interact with implantable medical devices and the second authentication credentials, and
a processor coupled to the memory and configured to perform actions comprising:
executing the second application using the instructions; and
transmitting the second authentication credentials to the external device.

14. The system of claim 13, wherein the memory of the external device has further stored thereon instructions for a first application configured to interact with implantable medical devices,
wherein the first authentication credentials are specific to the first application and identify at least one interaction capability of the first application with respect to the implantable medical device
wherein the second authentication credentials identify of at least one interaction capability of the second application with respect to the implantable medical device.

15. The system of claim 14, wherein the token or third authorization credentials identify the at least one interaction capability of the first application.

16. The system of claim 14, wherein the token or third authorization credentials identify the at least one interaction capability of the second application.

17. The system of claim 13, further comprising the implantable medical device configured for wireless communication with the external device and the second device.

18. The system of claim 17, wherein the implantable medical device is configured to limit authorized access to the second device based on identification of at least one interaction capability in the token or third authorization credentials.

19. The system of claim 1, wherein transmitting the token or third authorization credentials comprises transmitting the token or third authorization credentials to the implantable medical device directing the implantable medical device to authorize direct access to the implantable medical device by the second device.

20. A system, comprising:
the external device of claim 1; and
the implantable medical device configured for wireless communication with the external device.

* * * * *

UNITED STATES PATENT AND TRADEMARK OFFICE
CERTIFICATE OF CORRECTION

PATENT NO. : 12,402,004 B2
APPLICATION NO. : 17/513240
DATED : August 26, 2025
INVENTOR(S) : Sridhar Kothandaraman et al.

Page 1 of 1

It is certified that error appears in the above-identified patent and that said Letters Patent is hereby corrected as shown below:

On the Title Page

Item (73) For Assignee: Please delete "Boston Scient ation Corporation" and insert --Boston Scientific Neuromodulation Corporation--

Signed and Sealed this
Thirteenth Day of January, 2026

John A. Squires
*Director of the United States Patent and Trademark Office*